(12) United States Patent
Paufique

(10) Patent No.: US 11,311,596 B2
(45) Date of Patent: Apr. 26, 2022

(54) **ACTIVE INGREDIENT OBTAINED FROM *OPHIOPOGON JAPONICUS* FOR THE TREATMENT OF ATOPIC DERMATITIS**

(71) Applicant: Societe Industrielle Limousine D'Application Biologique, Objat (FR)

(72) Inventor: Jean Paufique, Objat (FR)

(73) Assignee: SOCIETE INDUSTRIELLE LIMOUSINE D'APPLICATION BIOLOGIQUE, Objat (FR)

( * ) Notice: Subject to any disclaimer, the term of this patent is extended or adjusted under 35 U.S.C. 154(b) by 423 days.

(21) Appl. No.: 16/069,265

(22) PCT Filed: Jan. 12, 2017

(86) PCT No.: PCT/FR2017/050070
§ 371 (c)(1),
(2) Date: Jul. 11, 2018

(87) PCT Pub. No.: WO2017/121965
PCT Pub. Date: Jul. 20, 2017

(65) Prior Publication Data
US 2019/0060390 A1    Feb. 28, 2019

(30) Foreign Application Priority Data

Jan. 12, 2016    (FR) ...................................... 1650228

(51) Int. Cl.
| | | |
|---|---|---|
| *A61K 36/8968* | (2006.01) | |
| *A61K 36/00* | (2006.01) | |
| *A61P 17/00* | (2006.01) | |
| *A61K 9/00* | (2006.01) | |
| *A61K 9/06* | (2006.01) | |
| *A61K 31/702* | (2006.01) | |

(52) U.S. Cl.
CPC ........ *A61K 36/8968* (2013.01); *A61K 9/0014* (2013.01); *A61K 9/0017* (2013.01); *A61K 9/06* (2013.01); *A61K 31/702* (2013.01); *A61P 17/00* (2018.01)

(58) Field of Classification Search
None
See application file for complete search history.

(56) References Cited

FOREIGN PATENT DOCUMENTS

| | | | |
|---|---|---|---|
| CN | 101757419 | A | 6/2010 |
| CN | 101904985 | A * | 12/2010 |
| CN | 101904985 | A | 12/2010 |
| CN | 102406570 | A | 4/2012 |
| CN | 103520475 | A | 1/2014 |
| CN | 103520572 | A | 1/2014 |
| CN | 103656323 | A | 3/2014 |
| CN | 103736068 | A | 4/2014 |
| FR | 2930729 | A1 | 11/2009 |
| KR | 2005014947 | A * | 2/2001 |
| KR | 20050014947 | A | 2/2005 |
| WO | WO0247704 | A1 | 6/2002 |
| WO | WO2014081715 | A1 | 5/2014 |

OTHER PUBLICATIONS

Yang (CN 101757419, See abstract, Jun. 30, 2010, in IDS) (Year: 2010).*
Limousine D Applic Biolog Dite (FR 2930729 See abstract Nov. 16, 2009, in IDS) (Year: 2009).*
Ando Y et al., "Skin-moisture-retaining agent for cosmetics—consists of sugars extracted from *Ophiopogon* and *Liriope* genus plants", WPI/Thomson, 1 page, Apr. 14, 1987, vol. 1987, No. 20, XP002511306.
Makino, T., "Effect of Bakumijiogan, an Herbal Formula in Traditional Chinese Medicine, on Atopic Dermatitis-Like Skin Lesions Inducted by Mite Antigen in NC/Jic Mice", Biol, Pharm. Bull, Sep. 3, 2008, pp. 2108-2113, vol. 31, No. 11.

* cited by examiner

*Primary Examiner* — Michael Barker
*Assistant Examiner* — Randall O Winston
(74) *Attorney, Agent, or Firm* — Greer, Burns & Crain, Ltd.

(57) ABSTRACT

Methods of treatment for atopic dermatitis in a human subject or animal, the methods comprising administering topically to the human subject or animal an active ingredient obtained from *Ophiopogon japonicus*.

12 Claims, 4 Drawing Sheets

Bacteria

ACTIVE INGREDIENT OBTAINED FROM *OPHIOPOGON JAPONICUS* FOR THE TREATMENT OF ATOPIC DERMATITIS

CROSS-REFERENCE TO RELATED APPLICATIONS

This application is a national stage application of PCT/FR2017/050070 filed Jan. 12, 2017 and claiming a benefit of priority from FR 1650228 filed Jan. 12, 2016, the entry disclosures of both applications are incorporated herein by reference.

TECHNICAL FIELD

This invention relates to the treatment of atopic dermatitis.

BACKGROUND

Atopic dermatitis, also called atopic eczema, is a chronic skin disease of genetic and environmental origin. It affects both humans and animals, mainly dogs and cats. In humans, atopic dermatitis is the most common form of dermatitis in children and can appear within the first few months of life. It affects 20% of children under 7 years old, is still at around 18% in children of 7 to 16 years old, and 3% of adults remain affected. The concept of chronicity and progression towards relapses is important. The prevalence (number of patients affected in the general population) of atopic dermatitis has tripled in 30 years in industrialized countries. This prevalence increases particularly depending on the environment, changes in life style and the increased hygiene in our industrialized societies. It has therefore become an emerging public health problem.

In animals, atopic dermatitis is a chronic and pruritic dermatitis that is multifactorial in origin. This disease results from complex interactions between factors of genetic predisposition and environmental factors. The first clinical signs of the disease in dogs or cats usually appear between 6 months and 3 years. The lesions mainly affect the face, the extremities, main skin folds and the abdomen. It is estimated to affect around 10 to 15% of the canine and feline populations. As animals are subjected to the same environmental aggressions as their masters, the prevalence of atopic dermatitis tends to increase in dogs as it does in humans, making this disease of primary concern for veterinary surgeons.

In humans, of whatever age, the appearance of atopic dermatitis is identical, with skin dryness due to the lack of protective hydrolipidic film and red, pruritic, thickened (lichenified) eczema plaques, possibly weeping.

This is a complex multifactorial disease, which makes it difficult to treat. All of the symptoms of the pathogenesis of atopic dermatitis (dry skin, red patches, itching, skin rashes and swelling, in periods of crisis and lull) are chiefly associated with the destruction of the skin barrier in the injured areas, but also in the uninjured areas, due to the poor synthesis of differentiation proteins such as cytokeratin 10, involucrin, loricrin and filaggrin.

The symptoms of atopic dermatitis are also characterized by an overexpression of the pro-inflammatory molecules such as interleukins (IL-) 4, 8, 13 and thymic stromal lymphopoietin (TSLP). In this vicious circle, the inflammatory response impacts on the synthesis of filaggrin. In the presence of Th2 cytokines, the differentiated keratinocytes significantly reduce the expression of the FLG (filaggrin) gene. The atopic inflammatory response is the central factor that increases the destruction of the skin barrier function.

Two groups of genes involved in atopic dermatitis have been identified: genes coding for the immune system and genes coding for epidermal structure proteins.

Canine and feline atopic dermatitis shares many clinical and immunological similarities with human atopic dermatitis. It is associated with an alteration of the skin barrier and in most cases with the production of IgE antibodies directed against environmental allergens (Marsella and Girolomoni "*Canine models of atopic dermatitis: a useful tool with untapped potential*," J Invest Dermatol, 2009 October; 129 (10):2351-7; Marsella et al "*Current evidence of skin barrier dysfunction in human and canine atopic dermatitis*" Veterinary Dermatology, 22, 239-248, 2011; Bizikowa et al "Review: Clinical and histological manifestations of canine atopic dermatitis," Vet Dermatol 2015; 26: 79-e24; Bizikowa et al "*Review: Role of genetics and the environment in the pathogenesis of canine atopic dermatitis*," Vet Dermatol 2015; 26: 95-e26).

By using an atopic canine experimental model, the overexpression of cytokines reflecting a Th2 bias in injured areas has been highlighted, in a manner similar to that observed in humans (Olivry et al, "*Early Activation of Th2/Th22 Inflammatory and Pruritogenic Pathways in Acute Canine Atopic Dermatitis Skin Lesions*," Journal of Investigative Dermatology, 2016).

The majority of existing products designed to treat atopic skins, in humans or animals, act on only one of the factors of the disease:
  either by limiting inflammation: this basically involves dermocorticoids (e.g. dexamethasone, synthetic corticoid) that temporarily calm the circle of inflammation,
  or by improving the skin barrier: this specifically involves emollients that seal the altered skin barrier in order mechanically to lock in the skin's moisture.

There are also ingredients from plants, but these basically act as anti-inflammatories or as agents that restructure the skin barrier.

SUMMARY

The purpose of the present invention is to propose an active ingredient obtained from a plant capable of acting on different factors of human or animal atopic dermatitis. To this end, the invention envisages an active ingredient obtained from *Ophiopogon japonicus* for use, by topical application onto the human or animal skin, in the treatment of atopic dermatitis.

*Ophiopogon japonicus* is a species of herbaceous perennial, low and rampant, with rhizomes of the Lilliacee family.

It is grown as an ornamental covering plant with tuberous rhizomes having a great many uses in traditional Chinese medicine.

The species originates from Japan and Korea and is also grown in Vietnam and China, particularly in the provinces of Sichuan, Zhejiang and Hubei. It is called Muguet du Japon in France and Mondo Grass, Fountain Plant, Monkey Grass or Dwarf Lilyturf in English.

The tuberous root is a few centimeters long; it is light yellow to yellowish-brown on the outside, with longitudinal creases. Its odor is weak, and its taste is slightly sweet and mucilaginous.

In traditional Chinese medicine, the root is known for "nourishing the Lungs and the Yin, nourishing the Stomach and producing Fluids, dispelling heat from the heart and calming the Spirit." The main therapeutic indications concern dry coughs, sore throats, insomnia, irritability, constipation and diphtheria, according to the 16th edition of the Japanese Pharmacopoeia.

The roots of *Ophiopogon japonicus* derive from varieties grown in China and Vietnam.

Extracts of *Ophiopogon japonicus* are known in cosmetics, specifically in patent FR2930729 as moisturizers acting on the rate of NMFs and on the formation of tight junctions between the layers. But moisturizing ingredients are not necessarily effective on the different markers of atopic dermatitis and, surprisingly, according to the invention, an active ingredient obtained from *Ophiopogon japonicus* can treat multiple factors of atopic dermatitis. It reduces the relapse rate, the severity, the intensity and the frequency of the flare-ups of attacks of atopic dermatitis; it reduces the extent of the eczema and improves the quality of life of patients and families or the quality of life of animals and their owners.

Its mode of action is based on inflammation (the inflammation markers and genes linked to inflammation), the skin barrier function (the epidermal cohesion markers and the genes associated with differentiation) and the organization and conformation of the epidermal lipids. It thus consolidates the epidermal structure and the integrity and resistance of the skin barrier, so as to limit the adhesion of bacteria to the skin. Further features and advantages will emerge from the following detailed description of the invention, in relation to the accompanying Figures.

DEFINITIONS

Figure 1A:
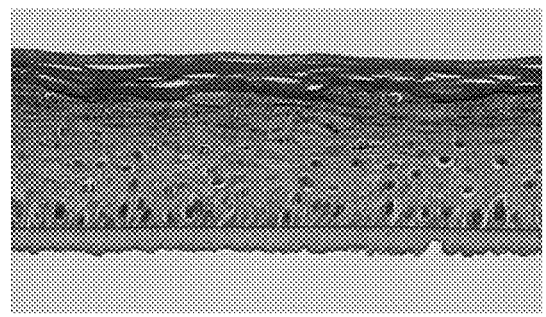
FIG. 1A represents the microscope image of a section of normal reconstructed human epidermis (corresponding to the results in Table 15—Normal REh—Control, General Morphology +++)
Figure 1B:
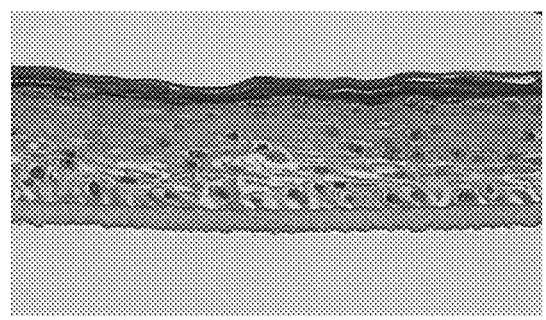
FIG. 1B represents the microscope image of a section of inflamed reconstructed human epidermis (corresponding to the results in Table 15—REhI—Control, General Morphology –)
Figure 1C:
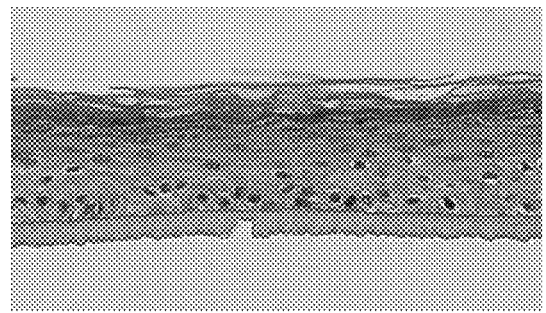
FIG. 1C represents the microscope image of a section of inflamed reconstructed human epidermis treated topically with an active ingredient according to the invention (corresponding to the results in Table 15—REhI—Example 1 at 1%, General Morphology ++)
Figure 1D:
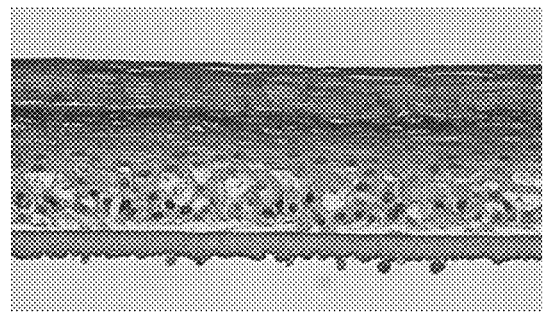
FIG. 1D represents the microscope image of a section of inflamed reconstructed human epidermis having an altered barrier (corresponding to the results in Table 15—REh-BAI—Control, General Morphology –)
Figure 1E:
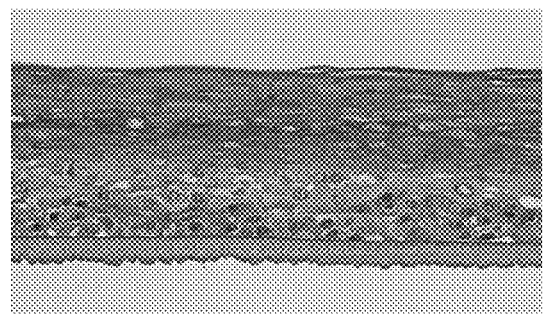
FIG. 1E represents the microscope image of a section of inflamed reconstructed human epidermis having an altered barrier treated topically with an active ingredient according to the invention (corresponding to the results in Table 15—REhBAI—Example 1 at 1%, General Morphology ++)

An "active ingredient" or "active" or "extract" within the meaning of the invention means at least one molecule, preferably an assembly of molecules having an effect on the skin cells.

An "active ingredient obtained from *Ophiopogon japonicus*" within the meaning of the invention means any molecule or mixture of molecules obtained from *Ophiopogon japonicus*. These may be native molecules of the plant or molecules obtained by any type of transformation of the native molecules of the plant, for example by hydrolysis. The active ingredient according to the invention is preferably a hydrolysate.

"Hydrolysate" means any extract of *Ophiopogon japonicus*, obtained by a method comprising at least one step of enzymatic or chemical hydrolysis of *Ophiopogon japonicus*, preferably at least one step of enzymatic hydrolysis.

"*Ophiopogon japonicus*" means all or part of the plant. This can be the whole plant or a part of the plant. Preferably, this means the tubers of *Ophiopogon japonicus*.

"Oligosaccharides" mean the oligomers formed by a number of monosaccharides by glycosidic bonding, the number of units of monosaccharides being fewer than 25 units.

"Polysaccharides" mean polymers consisting of several ores bound together by osidic bonds, the number of units of monosaccharides being greater than 25 units.

"Atopic skin" means the skin of a person or animal suffering from atopic dermatitis.

DETAILED DESCRIPTION OF THE INVENTION

The invention relates to an active ingredient obtained from *Ophiopogon japonicus* for use in the treatment of atopic dermatitis in humans or animals. The active ingredient is applied topically to the skin of the human or animal in order to act on all of the parameters of atopic dermatitis. It is used on atopic skins in order to:
  reduce the relapse rate,
  reduce the severity score of atopic dermatitis (SCORAD),
  reduce the intensity and frequency of flare-ups,
  reduce the extent of eczema,
  improve the quality of life index of patients and families or improve the quality of life of animals and owners.

These effects have been assessed by dermatologists, specifically on a panel of children with atopic skin.

The active ingredient according to the invention acts on:
  the skin barrier function, and/or
  skin inflammation, and/or
  skin microbiota,
preferably on all 3 of these three factors.

These efficacies with respect to the factors of atopic dermatitis are explained because the active ingredient according to the invention acts by:

reducing the inflammation of the skin cells, and/or
regularizing the cohesion of the skin cells, and/or
regularizing the differentiation of the skin cells, and/or
encouraging the organization and conformation of the epidermal lipids, and/or
encouraging epidermal construction, and/or
restoring the integrity and resistance of the barrier function of the skin, and/or
limiting the adhesion of bacteria to the skin.

Preferably, it has all of these effects.

In fact, the active ingredient according to the invention is capable of acting specifically:

on skin cell inflammation markers: in particular, it reduces the TSLP and IL-8 content of these cells, and/or
on the genes associated with the inflammation of skin cells: in particular, it normalizes the expression of the NELL2 gene and Tenascin C gene in these cells, and/or
on the epidermal cohesion markers: in particular, it increases claudine-1, and/or
on the skin cell differentiation markers: in particular, it increases the filaggrin, involucrin or loricrin in these cells, and/or
on the genes associated with the differentiation of the skin cells: in particular, it stimulates the expression of the FLG (filaggrin) gene and of the LOR (loricrin) gene and reduces the expression of the TGM1 (transglutaminase) gene in these cells, and/or
on the organization and conformation of epidermal lipids, and/or
on the morphological construction of the epidermis, and/or
on the integrity and resistance of the epidermal barrier, and/or
on the adhesion of bacteria to the skin: in particular, it limits the adhesion of *Staphylococcus aureus* to the skin.

Preferably, it has all of these effects.

These different efficacies can be demonstrated on any model of atopic skin, in particular on an inflamed cell model, on the specific models of reconstructed human epidermis known as REhI (inflamed human reconstructed epidermis) and RehBAI (inflamed human reconstructed epidermis having an altered skin barrier) as described in the publication by P. Rouaud-Tinguely et al. "*From the morphological to the transcriptomic characterization of a compromised three-dimensional in vitro model mimicking atopic dermatitis*" British Journal of Dermatology (2015) 173, pp 1006-1014 or on a model of a specific reconstructed canine epidermis such as that known as REcI (inflamed canine reconstructed epidermis).

The active ingredient obtained from *Ophiopogon japonicus* useful according to the invention in the treatment of atopic dermatitis is preferably an active ingredient obtained from *Ophiopogon japonicus* comprising sugars. Even more preferably, it comprises fructans, and more particularly it comprises at least 57% fructans by weight in relation to the weight of total sugars of the active ingredient, even more preferably at least 80%. Fructans are polysaccharides made up of fructose and glucose.

The sugars contained in the active ingredient are preferably formed by 45 to 80% fructose, by 20 to 50% glucose and by 0 to 5% galactose. These sugars can be in the form of monomers, oligomers and polymers. Mostly, the sugars contained in the active ingredient are oligo and polysaccharides of a molecular weight of less than 400 kDa in the form of fructans. Thus, preferably, the active ingredient according to the invention comprises oligo and polysaccharides of a molecular weight of less than 400 kDA in the form of fructans, representing at least 57% by weight of the sugars present in the active ingredient.

According to a particularly suitable variation, the active ingredient is obtained from *Ophiopogon japonicus* tubers.

According to one embodiment, the useful active ingredient according to the invention is in the form of a powder, in particular a light-colored powder, and has at least one, preferably all, of the following characteristics:

a dry matter content of between 900 and 1,000 mg/g,
a sugar content of between 500 and 800 mg/g, i.e. at least 50% sugars by weight in relation to the weight of dry matter.

The dry matter content can be measured by oven-drying a sample at 105° C. until a constant weight is achieved.

The total sugar content can be determined by the DUBOIS method over a range of fructose (Dubois M. et al., Analytical chemistry, 28, 3, 350-356, 1956).

The characterization of the molar mass of the carbohydrates present in the active ingredient of the present invention can be achieved by the HPLC method and the measurement of simple sugars by ionic liquid chromatography.

The molar masses of the carbohydrates are evaluated by comparing the retention times of the peaks detected in the samples of active ingredient with the retention times of standards injected beforehand.

The operating conditions are preferably as follows:
Equipment: Agilent 1100 Series HPLC
Columns: PL aquagel-OH C60, C40, C30 columns with a pre-column having the same characteristics
Elution method: isocratic
Mobile phase: $NaNO_3$ 0.3M+$NaH_2PO_4$-$2H_2O$ 0.01M pH7 buffer
Detection wavelengths: 254 nm and 280 nm UV The active ingredient according to the invention is preferably an active ingredient obtained in an aqueous medium from *Ophiopogon japonicus* tubers. "Obtained in an aqueous medium" means a medium that principally contains water, or a basic or acid aqueous medium. Specifically, it is not an oil or an essential oil.

Preferably, the active ingredient according to the invention is a hydrolysate of *Ophiopogon japonicus*, preferably an enzymatic hydrolysate.

According to a particularly suitable variation, the active ingredient according to the invention is a hydrolysate of *Ophiopogon japonicus* tubers, preferably an enzymatic hydrolysate of *Ophiopogon japonicus* tubers.

In particular, the useful active ingredient according to the invention can be obtained by implementing the following steps:

solubilization of *Ophiopogon japonicus* powder (preferably from tubers) in water in a proportion of at least 50 g/l,
at least one enzymatic hydrolysis of sugars,
separation of the soluble and insoluble phases, for example by decantation,
enzymatic inactivation by heat treatment of the soluble phase.

The enzymatic inactivation can be followed by one or more steps of filtration(s) and/or concentration. The active ingredient can be obtained in liquid form or in powder form by atomization or lyophilization. Preferably, it is atomized, in the presence of an atomization adjuvant such as maltodextrin, and used in powder form.

The parameters of the different steps must be adjusted in order to obtain active ingredients having the characteristics of the invention, in particular the presence of fructans having a molecular weight of less than 400 kDa.

The active ingredient according to the invention is preferably used in a dermatological composition, this composition comprising a dermatologically acceptable medium. These include compositions in different dosage forms, suitable for administration by dermal topical treatment.

These compositions can specifically be in the form of oil-in-water emulsions, water-in-oil emulsions, multiple emulsions (Water/Oil/Water or Oil/Water/oil) that may be microemulsions or nanoemulsions, or in the form of solutions, suspensions, hydrodispersions, aqueous gels or powders. They can be more or less fluid and have the appearance of a cream, a lotion, a milk, a serum, an ointment, a gel, a paste or a foam, or be in solid form.

Preferably they are in the form of a cream, a gel or an ointment.

They may be dermatological compositions comprising at least 0.05% of active ingredient obtained from *Ophiopogon japonicus*, according to the present invention, preferably between 0.05 and 1%.

These compositions comprise, apart from the active ingredient, a physiologically acceptable and dermatologically acceptable medium, i.e. that does not cause sensations of unacceptable discomfort for the user such as rashes, tautness or tingling. The compositions according to the invention can contain as a dermatologically acceptable adjuvant at least one compound chosen from:

- oils, that can be chosen specifically from silicone oils, linear or cyclic, volatile or non-volatile,
- waxes, such as ozokerite, polyethylene wax, bee's wax or carnauba wax,
- silicone elastomers,
- surfactants, preferably emulsifiers, whether non-ionic, anionic, cationic or amphoteric,
- thickening and/or gelling agents,
- humectants, such as polyols like glycerin,
- organic filters,
- inorganic filters,
- dyes, preservatives, fillers,
- tensors,
- sequestrants,
- and their mixtures, this list not being exhaustive.

Examples of such adjuvants are referred to specifically in the CTFA (*International Cosmetic Ingredient Dictionary and Handbook*, published by the Personal Care Products Council).

Clearly, a person skilled in the art would chose any additional, active or non-active, compounds and the quantity thereof, so that the advantageous properties of the mixture are not, or substantially not, altered by the envisaged addition.

The dermatological compositions comprising an active ingredient according to the invention can therefore be used to treat atopic dermatitis in humans or animals, particularly dogs or cats.

In order to illustrate these cosmetic effects on the skin, the following examples with their test results are provided.

EXAMPLES

Example 1: Active Ingredient According to the Invention

The active ingredient obtained from the tubers of *Ophiopogon japonicus* of Example 1 is characterized as follows:

Light-beige colored powder,
Dry matter: 960 mg/g,
Sugar content:
  Monosaccharides: 8% in relation to dry matter
  Oligo and polysaccharides: 88% in relation to dry matter
Mineral ash content: 2% in relation to dry matter
Protein content: 2% in relation to dry matter Example 2a: Dermatological Composition in the Form of Cream, Intended for Humans This formula is made up of a commercially available cream, Diprobase® Cream produced by Merck, to which has been added the active ingredient according to the invention of Example 1.

TABLE 1

| Brand Name | INCI Name | % incorporation of MP of | CAS No |
|---|---|---|---|
| Diprobase ® Cream | white soft paraffin | 99.95% | 8009-03-8 |
| | liquid paraffin | | 8012-95-1 |
| | cetostearyl alcohol | | — |
| | macrogol cetostearyl ether | | — |
| | Chlorocresol | | 59-50-7 |
| | sodium dihydrogen phosphate | | — |
| | sodium hydroxide | | — |
| | phosphoric acid | | — |
| | purified water | | 7732-18-5 |
| Active ingredient according to the invention | *Ophiopogon japonicus* root Extract | 0.05% | 952500-62-8 |

Example 2b: Dermatological Composition in the Form of Cream, Intended for Humans This formula is made up of a commercially available cream, Diprobase® Cream produced by Merck, to which has been added the active ingredient according to the invention of Example 1.

TABLE 2

| Brand Name | INCI Name | % incorporation of MP of | CAS No |
|---|---|---|---|
| Diprobase ® Cream | white soft paraffin | 99.9% | 8009-03-8 |
| | liquid paraffin | | 8012-95-1 |
| | cetostearyl alcohol | | — |
| | macrogol cetostearyl ether | | — |
| | Chlorocresol | | 59-50-7 |
| | sodium dihydrogen phosphate | | — |
| | sodium hydroxide | | — |
| | phosphoric acid | | — |
| | purified water | | 7732-18-5 |
| Active ingredient according to the invention | *Ophiopogon japonicus* root Extract | 0.1% | 952500-62-8 |

Example 2c: Dermatological Composition in the Form of Comfort Cream, Intended for Humans This formula is made up of a commercially available cream, Diprobase® Cream produced by Merck, to which has been added the active ingredient according to the invention of Example 1.

TABLE 3

| Brand Name | INCI Name | % incorporation of MP of | CAS No |
|---|---|---|---|
| Diprobase ® Cream | white soft paraffin | 99.7% | 8009-03-8 |
| | liquid paraffin | | 8012-95-1 |
| | cetostearyl alcohol | | — |
| | macrogol cetostearyl ether | | — |
| | Chlorocresol | | 59-50-7 |
| | sodium dihydrogen phosphate | | — |
| | sodium hydroxide | | — |
| | phosphoric acid | | — |
| | purified water | | 7732-18-5 |
| Active ingredient according to the invention | Ophiopogon japonicus root Extract | 0.3% | 952500-62-8 |

Example 3: Dermatological Composition in the Form of Lotion, Intended for Dogs The Composition of Example 3 is as follows:

| | |
|---|---|
| Water | 100% qs |
| Polyvinylpyrrolidone (PVP K90) | 2% |
| Glycerol | 5% |
| Butylene glycol | 5% |
| Polysorbate 20 | 3% |
| Paraffinum liquidum | 4% |
| Dimethicone copolyol | 2% |
| Hydroxyethyl cellulose | 0.2% |
| Preservative | 0.7% |
| Active ingredient of Example 1 | 0.5% |

Assessment of Efficacy on the parameters of Atopic Dermatitis

In Vivo Tests

The in vivo efficacy of an active ingredient obtained from *Ophiopogon japonicas* was tested during a study on children with atopic skin.

The inclusion criteria were:

Children from 4 months to 4 years having average to moderate atopic dermatitis,

Subjects having had at least one attack in the last 2 months,

Subjects having received a corticoid treatment to treat atopic dermatitis before the study, Subjects not using antibiotics, anti-histamines or calcineurin inhibitor for 3 weeks, Subjects not suffering from other skin conditions or chronic or progressive disease.

This randomized 2-month study consisted in a simple blind study of around one hundred subjects, having been treated either with a placebo formula or with a formula containing 0.3% active ingredient according to the invention (composition of Example 2c).

The subjects applied the product twice a day over their entire body.

The criteria for assessing efficacy were the IDQOL (Infant Dermatitis Quality of Life) Index, the DFI (Dermatitis Family Impact) Questionnaire and the SCORAD (Scoring Atopic Dermatitis) score. These criteria were assessed by a dermatologist on D0, D30 and D60.

The examination protocol is set out in Table 4 below:

TABLE 4

| | Examination 1 Pre-inclusion D-10 | Examination 2 Inclusion D0 | Examination 3 Follow-up D30 | Examination 4 End D60 |
|---|---|---|---|---|
| No of subjects included | 104 subjects | 90 subjects | 85 subjects | 68 subjects |
| Placebo Group | | 45 subjects | 43 subjects | 33 subjects |
| AI Group | | 45 subjects | 42 subjects | 35 subjects |
| No of subjects excluded | 0 | 14 subjects | +5 subjects | +17 subjects |

The skin exposure (SED) of atopic children to the active ingredient according to the invention is determined according to the following formula:

$$SED = [QA\ (g/d) \times 1{,}000\ mg/g \times C\ (\%)/100 \times DAp\ (\%)/100]/body\ weight$$

SED: Systemic Exposure Dosage

QA: Quantity of product applied via the skin

C: Concentration of substance studied in the finished product on the area of application DAp: Dermal Absorption expressed as a percentage of the test dose presumed to be applied in real conditions.

The children exposed were aged between 4 months and 4 years. In order to calculate exposure, the target population is the infant population. In fact, in order to maximize the value of exposure, infants represent the most sensitive population because they have a greater surface area/body weight ratio than that of an adult or children.

The quantity of product applied via the skin is 1.1 g/d for a body area of 2,200 cm$^2$ for a body product and weight of 3.4 kg.

As the skin absorption of the active ingredient is not fixed, a value of 50% will be selected, in accordance with the recommendations of the 9th Revision of the SCCS (September 2015).

It is assumed that the active ingredient will be used at a dose of 0.3% in the finished cosmetic product, which is equivalent to a concentration of 0.03% in the finished product.

$$SEDinfant = [1.1 \times 1{,}000 \times 0.03\%/100 \times 50\%/100]/3.4 = 0.048\ mg/kg\ cp/day$$

Effect on the Release Rate

The relapse rate was analyzed for both groups after 60 days. It is shown in Table 5 below.

TABLE 5

| | Relapse rate (%) | Rate without relapse (%) |
|---|---|---|
| Placebo | 40 | 60 |
| Formulation of Example 2c (Invention) | 21 | 79 |

It was observed that in the study conditions, after 60 days of treatment twice daily over the entire body, the relapse rate with the treatment according to the invention is twice as low as with the placebo treatment.

Effect on the Severity Score of Atopic Dermatitis (SCORAD)

The SCORAD or severity score of atopic dermatitis was created and validated in 1990 by a group of experts: the European Task Force of Atopic Dermatitis. It is a reference tool for doctors to monitor and assess the pathology. The SCORAD is defined by analyzing different items: average area of atopic lesions, erythema, edema/papules, weeping/scabs, excoriation, lichenification, dryness in the uninjured area, pruritic and insomnia.

An analysis of the SCORADs was performed by a dermatologist for patients who did not experience a relapse during the study (60% of the patients treated with the placebo, 79% of the patients treated with the AI).

The results are given in Table 6:

TABLE 6

| | Variation of the SCORAD (%) | |
|---|---|---|
| | D30/D0 | D60/D0 |
| Placebo | −11 | −13 |
| Formulation of Example 2c | −22 | −57 |

It was observed that in the study conditions, after 60 days of treatment twice daily over the entire body, the reduction in the severity score of atopic dermatitis observed by the dermatologist was −13% for the placebo and −57% for the formula containing an active ingredient obtained from *Ophiopogon japonicus*.

It was observed that in the study conditions, after 60 days of treatment, the severity score of the atopic dermatitis of the group treated with the active ingredient obtained from *Ophiopogon japonicus* was lower than that of the group treated with the placebo.

An analysis of the different items of the SCORAD was also performed after 30 days and after 60 days and is shown in Table 7:

TABLE 7

| | SCORAD at D30 | | SCORAD at D60 | |
|---|---|---|---|---|
| | Placebo | Active ingredient | Placebo | Active ingredient |
| Average area of atopic lesions | 0.54 | 0.56 | 0.54 | 0.22 |
| Erythema | 0.15 | 0.13 | 0.23 | 0.03 |
| Edema/papules | 0.12 | 0.03 | 0.00 | 0.03 |
| Weeping/scabs | 0.00 | 0.00 | 0.00 | 0.00 |
| Excoriation | 0.00 | 0.00 | 0.00 | 0.00 |
| Lichenification | 0.19 | 0.31 | 0.19 | 0.13 |
| Dryness in the uninjured areas | 0.50 | 0.38 | 0.35 | 0.28 |
| Pruritis | 0.58 | 0.31 | 0.62 | 0.25 |
| Insomnia | 0.54 | 0.41 | 0.31 | 0.16 |

A significant improvement was observed, particularly on the assessment parameters of erythema and pruritic.

General Assessment of Treatments by Dermatologists

Both treatments were assessed by dermatologists with respect to several criteria: soothing effect, reduction in the intensity of flare-ups, reduction in the frequency of flare-ups, good tolerance of the product and overall satisfaction with the product. The results after 30 days and 60 days of treatment are shown in Table 8 below:

TABLE 8

| | Positive assessment rate (%) | | | |
|---|---|---|---|---|
| | D30 | | D60 | |
| Dermatologists' assessment | Placebo | Active ingredient | Placebo | Active ingredient |
| Soothing effect | 98 | 95 | 85 | 97 |
| Reduction in intensity of flare-ups | 86 | 95 | 94 | 100 |
| Reduction in frequency of flare-ups | 86 | 88 | 94 | 100 |
| Good tolerance of the product | 100 | 95 | 91 | 97 |
| General satisfaction with the product | 86 | 90 | 91 | 97 |

It was observed that in the study conditions, after 30 days of treatment, the general assessment made by the dermatologists for the group treated with the active ingredient obtained from *Ophiopogon japonicus* was generally better than that of the group treated with the placebo.

This effect continued after 60 days of treatment; the active ingredient obtained from *Ophiopogon japonica* shows a soothing effect, reduces the intensity of flare-ups and the frequency of flare-ups, significantly better than those observed in the group treated with the placebo. It was satisfactory overall.

Effect on the Quality of Life

Atopic dermatitis is a chronic disease that has an impact on the quality of life and requires daily care. One of the important ways of monitoring the development of atopic dermatitis focuses on the parameters relating to quality of life: extent of eczema, impairment of the child quality of life index (IDQoL), impairment of the family quality of life index (DFIQ) and total quality of life index.

These parameters were assessed for patients who did not have a relapse during the study (placebo n=26 and AI n=32).

The results after 30 days and 60 days of treatment are shown in Table 9 below.

TABLE 9

| | D30/D0 | | D60/D0 | |
|---|---|---|---|---|
| Variation (%) | Placebo | Active Ingredient | Placebo | Active Ingredient |
| Extent of eczema | −27 | −50 | −27 | −89 |
| Child quality of life index (IDQoL) | 5 | −38 | −11 | −59 |
| Family Quality of life index (DFIQ) | −11 | −36 | −25 | −51 |
| Total quality of life index (Total QoL index) | −5 | −38 | −19 | −58 |

In the conditions of this study, after 30 days of treatment, an improvement in the quality of life QoL was observed for the group treated with the active ingredient obtained from *Ophiopogon japonicus*.

This effect continues after 60 days of treatment and the improvement is significantly visible with respect to the following parameters:
  Extent of the eczema: 89% reduction
  Improvement of the child quality of life index (IDQoL): 59% reduction
  Improvement of the family quality of life index (DFIQ): 51% reduction
  Improvement of the total quality of life index (Total QoL Index): 58% reduction.

General Assessment of Treatments by the Patients

The two treatments were assessed by the patients with respect to several criteria: delayed effect of relapse, daily comfort, product well tolerated, product pleasant to use, pleasure in using the product, product satisfactory, effectiveness of product. The results after 30 days and 60 days of treatments are given in Table 10 below:

TABLE 10

|  | Variation (%) | | | |
|---|---|---|---|---|
|  | D 30/D 0 | | D 60/D 0 | |
|  | Placebo | Active ingredient | Placebo | Active ingredient |
| Delayed effect of relapses | 63 | 76 | 79 | 91 |
| Daily comfort | 72 | 71 | 76 | 80 |
| Product well tolerated | 84 | 81 | 82 | 86 |
| Product pleasant to use | 65 | 69 | 70 | 74 |
| Pleasure in using the product | 67 | 76 | 73 | 77 |
| General satisfaction with the product | 72 | 86 | 79 | 89 |
| Is the product effective? | 81 | 95 | 76 | 97 |

In the conditions of this study, after 30 days of treatment, the general assessment of the patients in the group treated with the active ingredient obtained from *Ophiopogon japonicus* was generally better than that of the group treated with the placebo.

This effect continued after 60 days of treatment; the active ingredient obtained from *Ophiopogon japonicus* was significantly more satisfactory and effective compared to the placebo.

In conclusion, the dermatologists considered that the active ingredient obtained from *Ophiopogon japonicus* according to the invention had demonstrated a soothing effect and reduced the intensity and frequency of flare-ups. This product is therefore regarded as satisfactory overall. It lowers the relapse rate in atopic children and, after 60 days of treatment, significantly reduces by 25% the SCORAD index of atopic children.

The patients considered that the active ingredient according to the invention brings a comforting sensation. They perceived a general effectiveness and found the product to be satisfactory overall.

Above all, the active ingredient according to the invention reduced the extent of the eczema and improved the quality of life of the children and their families.

In Vitro and Ex Vivo Tests

In order to conduct in vitro and ex vivo tests, one cellular model, two specific reconstructed human epidermis (REh) models and one specific reconstructed canine epidermis (REc) model were used.

The 2D cellular model corresponds to a culture of normal human keratinocytes, subjected to an inflammation caused by an inflammatory cocktail (Poly I:C+TNFα+IL-4).

Normal human keratinocytes were grown in a complete culture medium for several days. The active ingredient according to the invention can be added to the cell culture medium.

The human reconstructed epidermal models have been described in the British Journal of Dermatology (2015) 173, 1006-1014.

The 3D model of inflamed reconstructed human epidermis (REhI) mimics the inflammation of human atopic dermatitis.

The 3D model of inflamed reconstructed human epidermis with an altered barrier (REhBAI) mimics the inflammation of human atopic dermatitis on an altered epidermis.

These 3D human models REhI and REhBAI were made as follows.

Normal human keratinocytes were grown in monolayers in a specific medium.

The REhI and REhBAI models were obtained by seeding normal human keratinocytes in culture inserts. The cells were grown in a complete medium for several days.

For the REhI Model

On the 14th day of growing the REhs, inflammation was caused by adding an inflammatory cocktail (Poly I/C+TNFα+IL-4+IL-13) to the culture medium for 2 additional days.

For the REhBAI Model

On the 15th day of growing the REhs, the REhs were topically treated with a solution of SDA (sodium dodecyl sulfate), in order to achieve a significant alteration of the skin barrier.

Inflammation was caused by the addition of an inflammatory cocktail (Poly I/C+TNFα+IL-4+IL-13) to the culture medium for one additional day.

These two human models were compared to a normal reconstructed epidermal model (REh), not having been treated either by the inflammatory cocktail or SDS. The active ingredient according to the invention could be added systemically to the culture medium of the REhs, or topically onto the reconstructed epidermis.

The 3D model of inflamed reconstructed canine epidermis (REcI) mimics the inflammation of canine atopic dermatitis; it was made as follows:

After seeding normal canine keratinocytes onto some culture inserts, the cells were grown in a complete medium for several days.

On the 11th day of growing the REcs, inflammation was caused by adding an inflammatory cocktail (Poly I/C+TNFα+IL-4+IL-13) to a culture medium for 2 additional days.

This model was compared to a normal reconstructed canine epidermal model (REc), not having been treated with the inflammatory cocktail. The active ingredient according to the invention can be added systemically to the culture medium of the REcs.

The effects of the active ingredient according to the invention were assessed:
  on the inflammation of atopic skin,
  on the skin barrier function,
  on the skin microbiota.

1/ Effect on the Inflammation of Atopic Skin

Skin is constantly subjected to signals from the environment. These signals will activate defense mechanisms, particularly immune mechanisms, which are manifested by an inflammatory reaction (Skabytska et al., "*The role of innate immune signaling in the pathogenesis of atopic dermatitis and consequences for treatments*," Semin. Immunopathol., 38, 29-43, 2016).

The skin immune system has two responses: innate and adaptive. The most effective reaction will be provided by a balance between these two responses whereas an imbalance causes atopic dermatitis. Basically, there are two lymphocyte subpopulations, Th1 and Th2 lymphocytes. Th1 lymphocytes encourage a so-called cellular response whereas Th2 lymphocytes tend towards a humoral response. When the Th2 prevails over Th1 response, the development of allergies is then encouraged because the production of immunoglobulin IgE is massively increased.

Due to the porosity of the epidermal barrier that occurs during this pathology, various exogenous elements such as allergens will be able to penetrate the epidermis. These allergens will lead to an immune response that is manifested by the secretion of cytokines by keratinocytes such as interleukins 33 and 25 but also thymic stromal lymphopoietin (TSLP). These cytokines then trigger a cascade of activation of different cells that leads towards a Th2 response. This response is characterized by the secretion of interleukins 4, 5, 13 and 31 but also by the production of IgE (Agrawal et al., "Skin barrier defects in atopic dermatitis," Current Allergy Asthma Rep., 14, 1-11, 2014). In return, these cytokines will have adverse effects on the barrier function by altering the efficient operation of epidermal differentiation.

Effect on Inflammation Markers

This study involves assessing the effect of an active ingredient obtained from *Ophiopogon japonicus* on the inflammation markers (IL-8 and/or TSLP) on the 2D cell model, the human models REhI and REhBAI and on the canine model REcI.

The active ingredient was added in a systemic treatment, i.e. at 0.10%, 0.15% or 0.25% directly to the culture mediums.

Amanaka et al (2011) and Stalder et al (2014) and Klukowska-Rötzler et al (2013) explained in their respective publications ("*The role of cytokines/chemokines in the pathogenesis of atopic dermatitis,*" Curr. Probl. Dermatol. 2011; 41:80-92, "*Fragility of epidermis and its consequence in dermatology,*" J Eur Acad Dermatol Venereol. 2014 June; 28 Suppl 4:1-18, "*Expression of thymic stromal lymphopoietin in canine atopic dermatitis,*" Vet. Dermatol. 2013 February; 24(1):54-9.e13-4) that human and canine atopic skins are characterized chiefly by an overexpression of the pro-inflammatory molecules such as IL-4, IL-8, IL-13 and thymic stromal lymphopoietin (TSLP).

The inflammatory response in the 2D cell model was assessed by measuring the thymic stromal lymphopoietin (TSLP) content released into the culture medium.

The inflammatory response in the 3D REhI and REhBAI human models and the 3D REcI canine model was assessed by measuring the IL-8 interleukin and/or thymic stromal lymphopoietin (TSLP) content released into the tissue subnatants.

The 2D culture medium and the subnatants of the REs were collected and kept at −20° C. The IL-8 and/or TSLP secretions were measured using an ELISA kit.

The results were compared to a cell culture or to the normal REh or REc models, not having been in contact with the inflammatory cocktail.

The results for the 2D model are given in Table 11, those for the human models in Table 12 and those for the canine model in Table 13.

TABLE 11

|  | TSLP (fg/µg proteins) | Efficacy/Inflamed Control (%) |
|---|---|---|
| Normal 2 D |  |  |
| Control Inflamed 2 D | 1 |  |
| Control | 633 |  |
| Example 1 at 0.15% | 434 | −31% |

It will be observed that the inflammatory cocktail caused an inflammatory effect (release of TSLP) in the cell model.

The active ingredient obtained from *Ophiopogon japonicus* reduced the inflammation caused by reducing by 31% the release of TSLP into the human keratinocyte cultures.

TABLE 12

|  | TSLP (pg/ml) | Efficacy/Inflamed Control (%) | IL-8 (pg/ml) | Efficacy/Inflamed Control (%) |
|---|---|---|---|---|
| Normal REh |  |  |  |  |
| Control | 0 |  | 24 |  |
| Example 1 at 0.25% | 0 |  | 24 |  |
| REhI |  |  |  |  |
| Control | 253 |  | 622 |  |
| Example 1 at 0.10% | 204 | −19% | 569 | −9% |
| Example 1 at 0.25% | 189 | −25% | 489 | −21% |
| REhBAI |  |  |  |  |
| Control | 30 |  | 794 |  |
| Example 1 at 0.10% | 15 | −50% | 621 | −22% |
| Example 1 at 0.25% | 14 | −54% | 603 | −24% |

It will be observed that the inflammatory cocktail caused an inflammatory effect (release of TSLP and IL-8) in the REhI and REhBAI models.

The active ingredient obtained from *Ophiopogon japonicus* had no negative effect on the normal REh model; it did not cause inflammation.

In the REhI model, the active ingredient obtained from *Ophiopogon japonicus* reduced the inflammation caused, reducing the TSLP content by 25% and the IL-8 content by 21%.

Similarly, in the REhBAI model, the active ingredient obtained from *Ophiopogon japonicus* reduced the inflammation caused, reducing the IL-8 content by 24%.

The use of an active ingredient obtained from *Ophiopogon japonicus* thus limits the inflammation in the injured areas and in the uninjured areas of atopic skins.

TABLE 13

|  | TSLP (pg/ml) | Efficacy/Inflamed Control (%) |
|---|---|---|
| Normal REc |  |  |
| Control | 15 |  |
| REcI |  |  |
| Control | 46 |  |
| Example 1 at 0.25% | 19 | −59% |

It will be observed that the inflammatory cocktail caused an inflammatory effect (release of TSLP) in the REcI model.

In the REcI model, the active ingredient obtained from *Ophiopogon japonicus* reduced the inflammation caused, reducing the TSLP content by 59%.

Effect on Genes Associated With Inflammation

This study involves assessing the effect of an active ingredient obtained from *Ophiopogon japonicus* on the genes associated with inflammation.

The active ingredient was added in a systemic treatment, i.e. at 0.10 and 0.25% directly to the REh culture medium.

In 2011, Kamsteeg established in her publication ("*Type 2 Helper T-Cell Cytokines induce morphologic and Molecular characteristics of Atopic Dermatitis in Human Skin Equivalent,*" Journal of Investigative Dermatology, 127, 1,786-1,789, 2007), that the key genes associated with inflammation are carbonic anhydrase II (CAII) and equivalent of the neural epidermal growth factor (NELL2) in the lesions of atopic skins compared to psoriasis.

The protocol of the present study is described below.

The total RNAs of the REs were extracted using an RNeasy kit. The quantification and assessment of the quality of the isolated RNAs were performed using a NanoDrop spectrophotometer and an Agilent bioanalyzer.

The fluorescence of the signals was detected by a specific scanner and the images were analyzed using a software program.

The analysis of the biological processes was performed on the transcriptomic data of the DAVID database.

1,730 genes of the 20,000 genes of the REhI model were overexpressed compared to the normal REh model, and 2,086 genes were underexpressed.

Four aspects grouped these 3,816 genes together: cell adhesion, cell migration, inflammation and epidermal cell differentiation. The genes (CXCL8, CA2, NELL2, TLR2, TLR3, NOTCH, STAT2, SPINK5, PLAUR and IL1A) associated with inflammation were overexpressed in REI.

The results obtained are given in Table 14 below.

TABLE 14

|  | NELL2 (%) | Efficacy/ Normal Control (%) | Tenascin C (TNC) (%) | Efficacy/ Normal Control (%) |
|---|---|---|---|---|
| Normal REh |  |  |  |  |
| Control | 100 |  | 100 |  |
| Example 1 at 0.25% | 98 |  | 122 |  |
| REhI |  |  |  |  |
| Control | 147 |  | 396 |  |
| Example 1 at 0.25% | 120 | −57% | 380 | −5% |
| Example 1 at 0.5% | 114 | −70% | 284 | −38% |

It will be observed that the inflammatory cocktail caused a marked inflammatory effect (overexpressions of the NELL2 and Tenascin C genes) in the REhI model.

In the REhI model, the active ingredient obtained from *Ophiopogon japonicus* reduced the expression of NELL2 and that of Tenascin C. In particular, the active ingredient tested at 0.5% reduced the expression of NELL2 by 70% and that of Tenascin C by 38%. The use of an active ingredient obtained from *Ophiopogon japonicus* thus limits the expression of the genes that cause the inflammation that is characteristic of atopic dermatitis.

2/ Effect on the Skin Barrier Function

The skin forms a barrier against environmental aggressions and the loss of water. In atopic dermatitis, a break in the barrier function has been demonstrated. Various parameters are altered, from structural proteins to lipids on passing through cell junctions.

Filaggrin is a protein essential for the formation of the stratum corneum. It is responsible for the reticulation of differentiation proteins such as keratins and subsequently the transformation of keratinocytes into corneocytes. This protein gives the stratum corneum its strength and consequently its barrier properties as regards the loss of water or external aggressions.

In the case of atopic dermatitis, it is known that the gene coding for filaggrin can have mutations causing a reduction in its synthesis. Beyond this mutation, the inflammation associated with this pathology also has negative consequences on the synthesis of filaggrin, but also on that of loricrin, involucrin and claudine-1. The integrity of the epidermal barrier is therefore altered, allowing the penetration of undesirable agents.

Effect on a Marker of Epidermal Cohesion

This study involves assessing the effect of an active ingredient obtained from *Ophiopogon japonicus* on the epidermal cohesion on the REhBAI model.

After 17 days of growing REhs with an altered barrier function, the epidermises were fixed, dehydrated with 4% paraformaldehyde and embedded in paraffin. 4 μm sections were made using a microtome. The morphological analysis of the sections was made by staining with HE (hematoxylin and eosin).

The immunohistofluorescence analysis of claudine-1 in the human 3D model was performed after incubation of a primary antibody and of a secondary antibody. Visualization was performed using a microscope connected to an image analysis system. The quantitative analysis was performed using MatLab® software.

The results were compared to a normal REh model, not having been in contact with the inflammatory cocktail.

The active ingredient of Example 1 was added as a topical treatment, i.e. at 0.075 and 0.150% directly to the REh culture medium.

The results obtained are given in Table 15 below.

TABLE 15

|  | Claudine-1 (%) | Efficacy of Claudine-1/Normal Control (%) |
|---|---|---|
| Normal REhBAI |  |  |
| Control | 100 |  |
| REhBAI |  |  |
| Control | 38 |  |
| Example 1 at 0.075% | 43 | 29% |
| Example 1 at 0.15% | 48 | 59% |

It will be observed that the inflammatory cocktail caused a limitation of cohesion by limiting the synthesis of claudine-1 in the REhBAI model.

In the REhBAI model, the active ingredient obtained from *Ophiopogon japonicus* maintained the synthesis of the epidermal cohesion marker. In particular, tested at 0.15%, it increased, topically, the synthesis of claudine-1 by 59%.

The use of an active ingredient obtained from *Ophiopogon japonicus* as a topical treatment thus increased the synthesis of the epidermal cohesion markers on atopic skins.

Effect on Epidermal Differentiation Markers

This study involves assessing the effect of an active ingredient obtained from *Ophiopogon japonicus* on the differentiation markers on the REhI model and/or on the REhBAI model.

All of the symptoms of atopic dermatitis are associated with the disruption of the skin barrier function of atopic patients. Several publications, such as Agrawal et al 2014 and Feingold et al 2014 ("*Role of lipids in the formation and maintenance of the cutaneous permeability barrier*" Biochim Biophys Act March 2014, 1841(3) 280-94), explain that the syntheses of differentiation proteins (loricrin, involucrin and/or filaggrin) are underexpressed in atopic skins.

The impact of the inflammatory response of the reconstructed epidermis was assessed on the differentiation markers, loricrin and/or filaggrin.

After 13 days of growing REcIs or 17 days of growing REhBAIs, the epidermises were fixed, dehydrated with 4% paraformaldehyde and embedded in paraffin. 4 μm sections were made using a microtome. The morphological analysis of the sections was made by staining with HE (hematoxylin and eosin).

The immunohistofluorescence analysis of filaggrin and/or loricrin in the human and canine 3D models was performed after incubation of a specific primary antibody and of a secondary antibody. Visualization was performed using a microscope connected to an image analysis system. The quantitative analysis was performed using MatLab® software.

The results were compared to a normal RE model, not having been in contact with the inflammatory cocktail.

The active ingredient of Example 1 was added:

either as a topical treatment, at 0.10% and 0.25%, directly to the REh and REc culture medium, or as a topical treatment, at 0.15%, directly to the REhs.

The results obtained on the human models are given in Tables 16 and 17 for the systemic treatments on the REhs or REcs (systemic treatment) and Table 18 for the topical treatments of the REhs, below.

Systemic Treatment

TABLE 16

|  | Fluorescence intensity of filaggrin/ surface (UA) | Capacity to maintain the synthesis of filaggrin (%) |
| --- | --- | --- |
| Normal REh |  |  |
| Control | 33 |  |
| Example 1 at 0.25% | 32 |  |
| REhI |  |  |
| Control | 13 |  |
| Example 1 at 0.10% | 18 | 25% |
| Example 1 at 0.25% | 22 | 45% |
| REhBAI |  |  |
| Control | 11 |  |
| Example 1 at 0.10% | 16 | 23% |
| Example 1 at 0.25% | 18 | 32% |

TABLE 17

|  | Fluorescence Intensity of loricrin/ surface (UA) | Capacity to maintain the synthesis of loricrin (%) |
| --- | --- | --- |
| Normal REc |  |  |
| Control | 19 |  |
| REcI |  |  |
| Control | 1 |  |
| Example 1 at 0.25% | 9 | 44% |

Topical Treatment

TABLE 18

|  | Fluorescence intensity of filaggrin/ surface (UA) | Capacity to maintain the synthesis of filaggrin (%) | Fluorescence Intensity of loricrin/ surface (UA) | Capacity to maintain the synthesis of loricrin (%) |
| --- | --- | --- | --- | --- |
| Normal REh |  |  |  |  |
| Control | 23 |  | 29 |  |
| REhBAI |  |  |  |  |
| Control | 17 |  | 0 |  |
| Example 1 at 0.15% | 32 | +250% | 6 | +21% |

It will be observed that the inflammatory cocktail caused a limitation of differentiation (inhibition of the synthesis of filaggrin and/or loricrin) in human and canine models, whether the treatment was systemic or topical.

The active ingredient had no effect on the normal REh model; it did not increase the differentiation markers.

In the human and canine models REhI and REcI, the active ingredient obtained from *Ophiopogon japonicus* maintained, systemically, the synthesis of the differentiation markers. In particular, tested at 0.25%, it increased, systemically, the synthesis of filaggrin by 45% in the human model and by 44% in the canine model.

In the human model REhBAI, the active ingredient according to the invention maintained, systemically or topically, the synthesis of the differentiation markers. In particular, tested at 0.15%, it increased, topically, the synthesis of loricrin and filaggrin.

The use of an active ingredient obtained from *Ophiopogon japonicus* as a systemic or topical treatment thus increases the synthesis of the differentiation markers on atopic skins, whether human or animal.

Effect on the Genes Associated With Epidermal Differentiation

This study involves assessing the effect of an active ingredient obtained from *Ophiopogon japonicus* according to the invention on the genes associated with differentiation.

The active ingredient was added as a systemic treatment, i.e. at 0.10 and 0.25% directly to the REh culture medium.

In 2005, Sugiura stated that, after analyzing 23,000 genes from the skin biopsies of patients suffering from atopic dermatitis by comparing them to controls, 10 genes showed important differences between the patients and the controls. The important modifications were the under-regulation of the genes coding for loricrin and filaggrin. (Sugiura et al. "*Large-scale DNA microarray analysis of atopic lesions shows an epidermis differentiation gene cluster in the alternative pathway and lack of protective gene expression in the cornified envelope*" BJD, vol 152, Issue 1, January 2015, p 146-149). In 2014, Zhang concluded in his publication ("*Screening for key genes associated with atopic dermatitis with DNA microarrays,*" Molecular Medicine Reports, March 2014, vol 9 Issue 3, p 1,049-1,055), that the key genes associated with atopic dermatitis are linked to differentiation: loricrin (LOR), keratin 17 (KRT17), small proline-rich repeat proteins (SPRRs) and involucrin (IVL).

The protocol of the study is described below.

The total RNAs of the REhs were extracted using an RNeasy kit. The quantification and assessment of the quality of the isolated RNAs were performed using a NanoDrop spectrophotometer and an Agilent bioanalyzer.

The fluorescence of the signals was detected by a specific scanner, SureScan Microarray, and the analysis of the images was performed by a software program. The analysis of the biological processes was performed on the transcriptomic data of the DAVID database.

1,730 genes of the 20,000 genes of the inflamed REh model were overexpressed compared to the normal RE model, and 2,086 genes were underexpressed.

Four aspects grouped these 3,816 genes together: cell adhesion, cell migration, inflammation and epidermal cell differentiation.

The genes (TGM1, S100A8, S100A9 and KLK7) associated with differentiation were overexpressed in inflamed REh.

The genes (FLG, LOR, KRT1, KRT10 and ITGA2) associated also with differentiation were under-regulated in inflamed REh.

The results obtained are given in Table 19 below:

TABLE 19

| | Filaggrin (%) | Efficacy/Normal Control (%) | Loricrin (%) | Efficacy/Normal Control (%) | TGM1 (%) | Efficacy/Normal Control (%) |
|---|---|---|---|---|---|---|
| Normal REh | | | | | | |
| Control | 100 | | 100 | | 100 | |
| Example 1 at 0.25% | 112 | | 103 | | 96 | |
| REhI | | | | | | |
| Control | 61 | | 52 | | 437 | |
| Example 1 at 0.25% | 74 | 33% | 63 | 23% | 385 | −15% |
| Example 1 at 0.5% | 88 | 69% | 71 | 40% | 318 | −35% |

It will be observed that the inflammatory cocktail caused a limitation of differentiation (under-expression of the FLG gene, filaggrin and the LOR gene, loricrin, and over-expression of the TGM1 gene, transglutaminase 1) in the REhI model.

The use of an active ingredient obtained from *Ophiopogon japonicus* therefore increased the expression of the filaggrin and loricrin genes and reduced the expression of the transglutaminase 1 gene, associated with differentiation.

Effect on the Organisation and Conformation of Epidermal Lipids

In atopic dermatitis, several mechanisms involved in the process of maturation of epidermal lipids are altered. The lamellar bodies, organelles responsible for storing lipid precursors, have a defect with respect to maturation and the release of their contents. The ceramide concentration is reduced due to an abnormal activity of the enzymes of the lipid metabolism. Moreover, beyond the quantitative aspect, a reduction in the length of the chains of fatty acids and ceramides is observed resulting in an increase in the permeability of the epidermal barrier. Lastly, the organization of the lipids in relation to one another is also altered (Elias et al. "*Lipid abnormalities and lipid-based repair strategies in atopic dermatitis*" Biochimica et Biophysica Acta, 1841, 323-330, 2014; Van Smeden et al. "*The important role of stratum corneum lipids for the cutaneous barrier function*," Biochimica et Biophysica Acta, 1841, 295-313, 2014). In order to assess directly in vivo the influence of the active ingredient according to the invention on the lipid component, a study aimed at establishing the molecular signature of atopic skins was made by Raman microspectroscopy. This study, conducted both on volunteers suffering from atopic dermatitis and on healthy volunteers, demonstrated a disruption of the intramolecular conformation of the lipids as well as a modification of their organization in atopic subjects.

In a second step, the effect of the active ingredient according to the invention on the organization and conformation of the lipids was measured in vivo after application twice daily for 60 days. This study was conducted on 40 adult volunteers suffering from slight to moderate atopic dermatitis, divided into two groups: one treated with a placebo formula, the other with a formula containing the active ingredient according to the invention at 0.5%.

The spectral bands characteristic of the organization and conformation of the lipids were studied via the following descriptors:

the vCC trans/vCC gauche ratio provides information on the intramolecular conformation of the lipids. The predominance of the trans conformation is linked to greater compactness of the skin barrier. By contrast, a larger quantity of gauche conformers demonstrates a weakening of compactness of the skin lipid structures.

The $v_{asym}CH_2/v_{sym}CH_2$ ratio is an indicator of the lateral organization of the lipids of the stratum corneum. High values of this ratio are associated with an orderly organization. A reduction of this ratio is associated with a loss of organization.

The experimental system used to measure these parameters was a Raman microspectroscopy system. This comprises a confocal Raman probe connected to a dispersive Raman spectrometer, the spectrometer is equipped with a CCD (Coupled Charge Detector). The acquisition system is controlled by a software program.

The Raman profiles are recorded when collecting spectra from −10 μm above the surface of the skin and down to a depth of 40 μm.

This study was conducted in partnership with the teams of Professors Arlette Baillet-Guffroy (Analytical Chemistry Group, EA4041, Université Paris-Sud 11) and Michel Manfait (MéDIAN-CNRS UMR 7369, Faculty of Pharmacy at Reims Champagne-Ardenne University).

TABLE 20

| Variation/D 0 | Conformation of lipids (vCC trans/vCC gauche Ratio) | Organization of lipids (vasymCH2/vsym CH2 Ratio) |
|---|---|---|
| Placebo group | −42.5% | −15.3% |
| Group treated with the Formula containing the active ingredient according to the invention | +71.8% | −4.1% |

Under the conditions of this study, after 2 months of treatment, the formula containing the active ingredient according to the invention at 0.5% allowed the quality of the skin barrier to be preserved.

For the subjects who used the active formula:
the predominance of the trans conformation was observed (increase in the trans/gauche ratio) and was linked to greater compactness of the skin barrier;
the organization of the lipid matrix of the stratum corneum was maintained in its optimal state over time ($v_{asym}CH_2/v_{sym}CH_2$ ratio virtually unchanged).

For subjects who applied the placebo formula:

a larger quantity of gauche conformers was observed (reduction of the trans/gauche ratio) overtime, demonstrating a weakening of the compactness of the skin lipid structures;

a significant fall in the organization of the lipid matrix was observed over time (reduction in the $v_{asym}CH_2/v_{sym}CH_2$ ratio).

Assessment of the Integrity and Resistance of the Epidermal Barrier

The integrity and resistance of the epidermal barrier can be demonstrated by several studies:

visualizing the general state of the epidermal structure of a reconstructed epidermis, quantifying the integrity of the epidermal barrier by assessing the non-penetration of a dye or quantifying the vesicles present in the epidermis, measuring the transepithelial resistance characterizing skin resistance.

General Visualization of the Epidermal Structure

This study involves assessing the effect of an active ingredient obtained from *Ophiopogon japonicus* on the epidermal structure in the human models REhI and REhBAI and in the canine model REcI.

The epidermal structure in the inflamed 3D models was assessed by morphological analysis of the epidermal sections after staining with HE (hematoxylin and eosin). After 17 days of growing REhs or 13 days of growing REcs, the epidermises were fixed, dehydrated with 4% paraformaldehyde and embedded in paraffin. 4 µm sections were made using a microtome. The morphological analysis of the sections was made using HE stain. Visualization was performed using a microscope connected to an image analysis system.

The active ingredient was added as a topical treatment, at 0.05 and 0.10% to a cosmetic formula on human epidermises and at 0.25% on canine epidermises. The placebo formula was also tested.

The results are given in Table 21 below and in FIGS. 1A to 1E and those for the canine model are given in Table 22.

TABLE 21

| | General morphology |
|---|---|
| Normal REh | |
| Control | +++ |
| Placebo | +++ |
| Example 2b containing 0.1% of the AI | +++ |
| REhI | |
| Control | − |
| Placebo | − |
| Example 2a containing 0.05% of the AI | + |
| Example 2b containing 0.1% of the AI | ++ |
| REhBAI | |
| Control | − |
| Placebo | − |
| Example 2a containing 0.05% of the AI | + |
| Example 2b containing 0.1% of the AI | ++ |

+++ means normal reconstructed epidermis, compact epidermal layers
++ means altered reconstructed epidermis, less compact epidermal layers
+ means altered reconstructed epidermis, much less compact epidermal layers
− means very altered reconstructed epidermis, non-compact epidermal layers or spongy appearance of the epidermis

TABLE 22

| | General Morphology |
|---|---|
| Normal REc | |
| Control | +++ |
| REcI | |
| Control | − |
| Example 2a containing 0.25% of the AI | ++ |

+++ means normal reconstructed epidermis, compact epidermal layers
++ means altered reconstructed epidermis, less compact epidermal layers
+ means altered reconstructed epidermis, much less compact epidermal layers
− means very altered reconstructed epidermis, non-compact epidermal layers or spongy appearance of the epidermis It will be observed that the inflammatory cocktail caused serious disruption of the global morphology of the reconstructed epidermis, whether human or canine. It appears altered and spongy in the control of the inflamed RE models.

By contrast, the active ingredient obtained from *Ophiopogon japonicus* used topically protected the general morphology of the RE in the inflamed REc and REh models.

The use of an active ingredient obtained from *Ophiopogon japonicus* consequently improves, when applied topically, the general morphology of the epidermises on human or canine atopic skins.

Assessing the Integrity of the Epidermal Barrier

This study involves assessing the effect of an active ingredient obtained from *Ophiopogon japonicus* according to the invention on the integrity of the epidermal barrier of the REhBAI human model.

Two tests enable the integrity of the barrier function to be visualized:

The use of a fluorescent probe, lucifer yellow dye. The more intense the color, the greater the epidermal barrier.

The use of epidermal spongiosis, which enables the vesicles in the epidermis to be quantified. The more epidermal spongiosis is quantified, the more the presence of vesicles is observed and the more the epidermal barrier is altered.

After several days of growing the REhs, lucifer yellow was applied to the reconstructed epidermises. After incubation at 37° C., the epidermises were rinsed with PBS buffer and fixed with PFA. 4 µm sections were then made using a microtome.

Visualization of the integrity of the skin barrier was performed using a microscope connected to an image analysis system.

The thickness of the epidermises and the penetration of lucifer yellow were measured on the histological sections made.

The active ingredient was added as a topical treatment, at 0.5 and 1% in a cosmetic formula to the epidermises. The placebo formula was also tested.

Figure 2A:
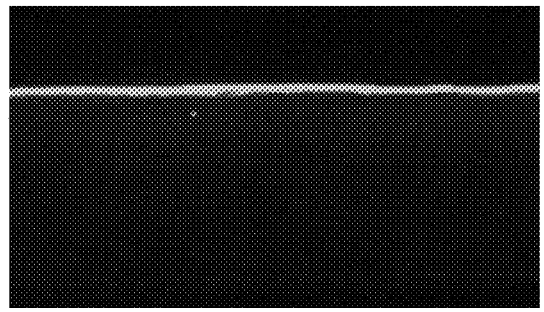
FIG. 2A represents the microscope image of a section of normal reconstructed human epidermis marked with a fluorescent probe (lucifer yellow) (corresponding to the results in Table 16—REhBAI—Normal REh –Control, Penetration Measurement of lucifer yellow: 4)
Figure 2B:
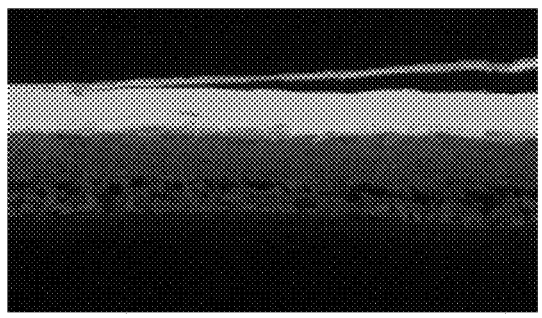
FIG. 2B represents the microscope image of a section of inflamed reconstructed human epidermis having an altered barrier marked with a fluorescent probe (lucifer yellow) (corresponding to the results in Table 16—REhBAI—Control, Penetration Measurement of lucifer yellow: 85)
Figure 2C:
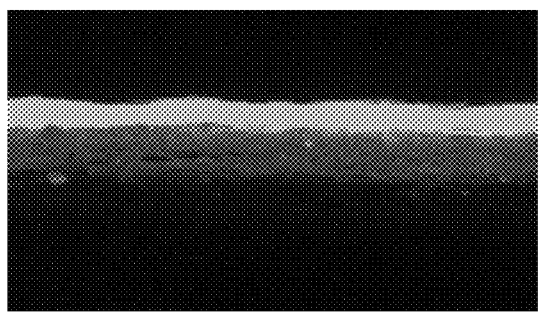
FIG. 2C represents the microscope image of a section of inflamed reconstructed human epidermis having an altered barrier treated topically with an active ingredient according to the invention, marked with a fluorescent probe (lucifer yellow) (corresponding to the results in Table 16—REhBAI—Example 1 at 1%, Penetration Measurement of lucifer yellow: 51)

The results are given in Table 23 below and in FIGS. 2A to 2C.

TABLE 23

| | Measurement of penetration of lucifer yellow (µm) | Efficacy/ REhBAI Control | Measurement of epidermal spongiosis (%) | Efficacy/ REhBAI Control |
|---|---|---|---|---|
| Normal REh | | | | |
| Control | 4 | | 0 | |
| Placebo | 4 | | | |
| Example 2b containing 0.1% AI | 4 | | | |

TABLE 23-continued

| REhBAI | Measurement of penetration of lucifer yellow (μm) | Efficacy/ REhBAI Control | Measurement of epidermal spongiosis (%) | Efficacy/ REhBAI Control |
|---|---|---|---|---|
| Control | 85 | | 9.6 | |
| Placebo | 65 | −25% | | |
| Example 2a containing 0.05% AI | 56 | −36% | | |
| Example 2b containing 0.075% AI | | | 1.2 | −88% |
| Example 2b containing 0.10% AI | 51 | −42% | | |
| Example 2b containing 0.15% AI | | | 0.4 | −96% |

The degradation of the integrity of the epidermal barrier was very great in the RehBAI model and the penetration of the lucifer yellow dye and measurement of epidermal spongiosis was increased.

It will be observed that the active ingredient obtained from *Ophiopogon japonicas* limits the penetration of lucifer yellow and the presence of epidermal spongiosis, and thus protects the integrity of the epidermal barrier in the REhBAI model.

The use of an active ingredient obtained from *Ophiopogon japonicas* consequently protects, as a topical or systemic application, the integrity of the epidermal barrier of atopic skins.

Assessment of Skin Barrier Resistance

This study involves assessing the resistance of the skin barrier of a reconstructed epidermis with and without the presence of an active ingredient obtained from *Ophiopogon japonicus* according to the invention.

Transepithelial resistance is measured and expressed in $\Omega cm^2$.

The results are given in Table 24 below.

TABLE 24

| REhBAI | Transepithelial Resistance ($\Omega$ cm$^2$) | Efficacy/ REhBAI Control |
|---|---|---|
| Control | 317 | |
| Example containing 0.075% AI | 478 | 51% |
| Example containing 0.15% AI | 510 | 61% |

It will be observed that the active ingredient obtained from *Ophiopogon japonicus* increases the transepithelial resistance in the REhBAI model.

The use of an active ingredient obtained from *Ophiopogon japonicus* consequently protects, as a topical or systemic application, the integrity of the epidermal barrier of atopic skins.

3/ Effect on the Skin Microbiota

In direct contact with the environment, the skin is colonized by a large number of microorganisms: bacteria, yeasts, fungi, viruses and mites. Existing knowledge shows that most of these microorganisms are harmless to humans. The host and the microbiota live in symbiosis (Salava et al., "*Role of the skin microbiome in atopic dermatitis*," Clinical and translational allergy, 4, 1-6, 2014).

Over the last five years, research on microbiota has increased significantly. This increase is explained by great technical advances achieved in bacterial analysis tools. It has thus been possible to establish the global mapping of the skin microbiota. Although harmless to individuals, the microbiota does, however, have an impact on the skin. In fact, by activating the immune response, the commensal germs enable the skin to produce antimicrobial peptides (cathelicidins, β-defensins) that will prevent invasion by undesirable bacteria. These bacteria also activate the Th1 response to the detriment of the Th2 response, a path involved in the development of atopic dermatitis (Powers et al., "*Microbiome and pediatric atopic dermatitis*," Journal of Dermatology, 42, 1,137-1,142, 2015). These data describe at what point the microbiota is important for maintaining a healthy skin.

In the case of atopic dermatitis, the skin microbiota is drastically modified. The injured areas have a reduced microbial diversity benefiting a proliferation of the *Straphylococcus* genus. Two types of staphylococci are described as having a strong presence: *Staphylococcus aureus* and *Staphylococcus epidermidis* against only 5 to 20% of healthy areas. This abnormal colonization results in a reduction in immune defenses that accompanies this pathology and that encourages the implantation of undesirable bacteria. In return, *Staphylococcus aureus* will accentuate the faults of barrier function by secreting superantigens or toxins that will stimulate the proliferation of T lymphocytes and further reduce the production of antimicrobial peptides (Williams et al., "The Role of the Skin Microbiome in Atopic Dermatitis," Curr Allergy Asthma Rep, 15, 2-10, 2015, Thomas et al., "*The microbiome and atopic eczema: more than skin deep*," Australian journal of Dermatology, 2016).

The bacterial component of the skin therefore constitutes an important parameter in the development of atopic dermatitis. To date, some treatments are described as capable of rebalancing the bacterial ecology with respect to lesions. In the same way, therapies that improve the skin microbiota of atopic skins are associated with an improvement in the clinical picture of patients (Flores et al., "*Microbiome of affected and unaffected skin patients with atopic dermatitis before and after emollient treatment*," Journal of drugs in dermatology, 13, 1365-1371, 2014; Seité et al., "*Barrier function and microbiotic dysbiosis in atopic dermatitis*," Clinical, cosmetic and investigational dermatology, 8, 479-483, 2015).

Assessment of the Formation of Biofilm Induced by *Staphylococcus aureus*

The effect of the active ingredient according to the invention on the skin microbiota was assessed in vitro on human reconstructed epidermises after the application of a suspension of *Staphylococcus aureus*.

Normal human reconstructed epidermises were topically pre-treated for 24 hours with the active ingredient according to the invention at 0.15% (V/V), and then treated with a suspension of *S. aureus* ($10^6$ CFU/mL) for 24 hours.

Figure 3A:
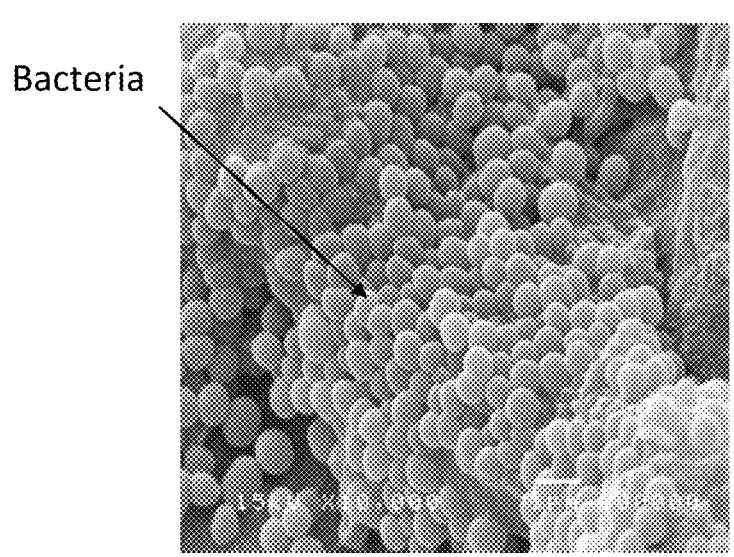
FIG. 3A represents the image of the biofilm of *Straphylococcus aureus* formed on the control reconstructed epidermis subjected to bacterial aggression.
Figure 3B:
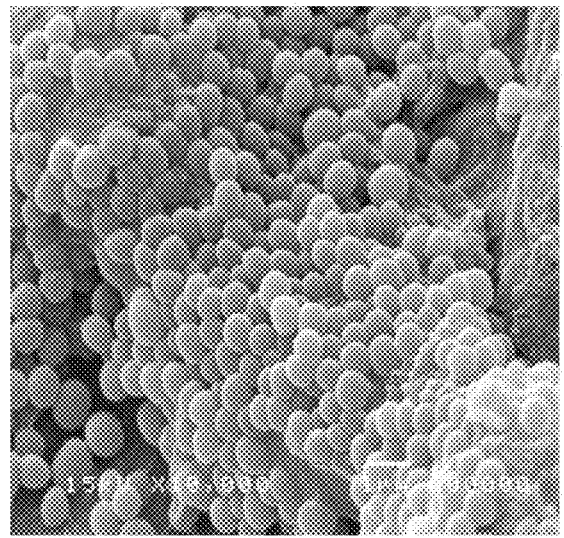
FIG. 3B represents the image of the biofilm of *Straphylococcus aureus* formed on the reconstructed epidermis treated by the active ingredient according to the invention subjected to bacterial aggression.

The adhesion/colonization by *Staphylococcus aureus* (biofilm) was visualized under a scanning electron microscope, as shown in FIGS. 3A (Formation of biofilm induced by *S. aureus* on the control REh) and 3B (formation of biofilm induced by *S. aureus* on the REh treated by the active ingredient according to the invention).

TABLE 25

|  | Control REh | REh treated with 0.15% active ingredient according to the invention |
|---|---|---|
| Formation of biofilm | +++ | + |

Applied topically at 0.15% to normal human reconstructed epidermises subjected to bacterial aggression, the active ingredient according to the invention limits the adhesion of *Staphylococcus aureus* and subsequently the formation of biofilm.

The invention claimed is:

1. A method of treating atopic dermatitis in a human subject or animal in need thereof, the method consisting of applying topically onto the atopic skin of the human subject or animal an active ingredient in a composition, wherein the active ingredient is a hydrolysate of *Ophiopogon japonicus* tubers containing sugars, and wherein applying topically onto the skin the active ingredient acts on the skin barrier function, and skin inflammation, and skin microbiota.

2. The method of claim 1, wherein the active ingredient is applied on human or animal atopic skins.

3. The method of claim 1, wherein the animal is a dog or cat.

4. The method of claim 1, wherein the active ingredient treats atopic dermatitis by acting on:
   the skin barrier function, and/or
   skin inflammation, and/or
   skin microbiota.

5. The method of claim 4, wherein the active ingredient acts:
   on the cell inflammation markers, and/or
   on the genes associated with the inflammation of skin cells, and/or
   on the cohesion markers, and/or
   on the skin cell differentiation markers, and/or
   on the genes associated with the differentiation of the skin cells, and/or
   on the organization and conformation of epidermal lipids, and/or
   on the morphological construction of the epidermis, and/or
   on the integrity and resistance of the epidermal barrier, and/or
   on the adhesion of bacteria to the skin.

6. The method of claim 5, wherein the active ingredient treats atopic dermatitis by acting:
   by reducing the TSLP or IL-8 content in the skin cells, and/or
   by normalizing the expression of the NELL2 gene and Tenascin C gene in the skin cells, and/or
   by increasing the claudine-1 in the skin cells, and/or
   by increasing the filaggrin, loricrin or involucrin in the skin cells, and/or
   by stimulating the expression of the filaggrin gene or loricrin gene in the skin cells, and/or
   by reducing the expression of the TGM1 (transglutaminase 1) gene in the skin cells, and/or
   by limiting the adhesion of the *Staphylococcus aureus* to the skin.

7. The method of claim 1, wherein the active ingredient comprises at least 50% sugar by weight in relation to the total weight of dry matter.

8. The method of claim 1, wherein the active ingredient comprises fructans.

9. The method of claim 1, wherein the active ingredient comprises at least 57% fructans by weight in relation to the weight of total sugars of the active ingredient.

10. The method of claim 1, wherein the active ingredient is an enzymatic hydrolysate of *Ophiopogon japonicus*.

11. The method of claim 1, wherein the active ingredient is applied in a dermatological composition containing at least 0.05% of the active ingredient.

12. The method of claim 1, wherein the active ingredient is in a dermatological composition in the form of a cream, gel, lotion, shampoo or ointment.

* * * * *